(12) United States Patent
Drebing et al.

(10) Patent No.: US 11,313,854 B2
(45) Date of Patent: *Apr. 26, 2022

(54) PATTERNED MEMBRANE STRUCTURE

(71) Applicant: SARTORIUS STEDIM BIOTECH GMBH, Gottingen (DE)

(72) Inventors: Susanne Drebing, Hardegsen (DE); Alfons Kesting, Beuren (DE); Dieter Melzner, Gottingen (DE); Denise Van Rossum, Adelebsen (DE)

(73) Assignee: SARTORIUS STEDIM BIOTECH GMBH

( * ) Notice: Subject to any disclaimer, the term of this patent is extended or adjusted under 35 U.S.C. 154(b) by 0 days.

This patent is subject to a terminal disclaimer.

(21) Appl. No.: 15/774,143

(22) PCT Filed: Jul. 19, 2016

(86) PCT No.: PCT/EP2016/001258
§ 371 (c)(1),
(2) Date: May 7, 2018

(87) PCT Pub. No.: WO2017/084728
PCT Pub. Date: May 26, 2017

(65) Prior Publication Data
US 2018/0328918 A1    Nov. 15, 2018

(30) Foreign Application Priority Data
Nov. 19, 2015    (EP) .................................... 15003304

(51) Int. Cl.
   *G01N 33/52*    (2006.01)
   *G01N 33/543*    (2006.01)
   (Continued)

(52) U.S. Cl.
   CPC .......... *G01N 33/525* (2013.01); *G01N 33/52* (2013.01); *G01N 33/543* (2013.01);
   (Continued)

(58) Field of Classification Search
   None
   See application file for complete search history.

(56) References Cited

U.S. PATENT DOCUMENTS 3,520,416 A * 7/1970 Keedwell ............. B01D 36/001
                                                210/490
5,998,221 A    12/1999 Malick et al.
   (Continued)

FOREIGN PATENT DOCUMENTS

CN    1768267    1/2009
DE    20218984    5/2003
   (Continued)

OTHER PUBLICATIONS

Patent Cooperation Treaty (PCT), International Search Report and Written Opinion for Application PCT/EP2016/001258 filed Jul. 19, 2016, dated Sep. 28, 2016, International Searching Authority, EP.

*Primary Examiner* — Brian R Ohara
(74) *Attorney, Agent, or Firm* — McDonald Hopkins LLC

(57) ABSTRACT

The present invention relates to a patterned membrane structure comprising a microporous membrane layer, wherein the microporous membrane layer includes a plurality of flow lanes, the flow lanes are separated by hydrophobic separation channels, and the flow lanes and hydrophobic separation channels form a repetitive pattern; and a method for manufacture of the patterned membrane structure. The patterned membrane structure according to the present invention represents an industrial scale precursor of membranes such as a multiparameter lateral flow membrane comprising separated flow lanes.

18 Claims, 10 Drawing Sheets

(51) Int. Cl.
    *B01D 61/18*     (2006.01)
    *B01D 69/12*     (2006.01)

(52) U.S. Cl.
    CPC ....... *G01N 33/54366* (2013.01); *B01D 61/18* (2013.01); *B01D 69/12* (2013.01); *B01D 2323/30* (2013.01)

(56) References Cited

U.S. PATENT DOCUMENTS

| | | | |
|---|---|---|---|
| 9,970,933 B2* | 5/2018 | Kim | G01N 33/56916 |
| 10,031,100 B2 | 7/2018 | Johnson et al. | |
| 2004/0240137 A1 | 12/2004 | Fisher-Fruhholz | |
| 2006/0246599 A1 | 11/2006 | Rosenstein et al. | |
| 2007/0042444 A1 | 2/2007 | Niskanen et al. | |
| 2009/0298191 A1 | 12/2009 | Whitesides et al. | |
| 2010/0159599 A1* | 6/2010 | Song | A61F 13/42 436/39 |
| 2011/0124130 A1 | 5/2011 | Wagner et al. | |
| 2015/0241425 A1* | 8/2015 | McKee | G01N 33/54366 506/9 |

FOREIGN PATENT DOCUMENTS

| | | | |
|---|---|---|---|
| DE | 102005014691 | 10/2006 | |
| DE | 102007036906 | 11/2008 | |
| EP | 1990638 | 11/2008 | |
| EP | 2031376 | 10/2011 | |
| EP | 2955519 | 8/2019 | |
| JP | 2012098237 | 10/2014 | |
| WO | 200232533 | 4/2002 | |
| WO | WO-2013051890 A2 * | 4/2013 | ....... G01N 33/54393 |
| WO | 2013051890 | 7/2013 | |

* cited by examiner (A)

5 mm (B)

(A)

(B)

(C)

A.

B.

C.

A

B.

4 mm

PATTERNED MEMBRANE STRUCTURE

CROSS-REFERENCE TO RELATED APPLICATION

This application is a 35 U.S.C. 371 national stage filing of PCT Application No. PCT/EP2016/001258 filed on Jul. 19, 2016, entitled "PATTERNED MEMBRANE STRUCTURE," which claims priority to European Patent Application No. 15003304.1, filed on Nov. 19, 2015, each of which are incorporated by reference herein in their entirety.

FIELD OF INVENTION

The present invention relates to a patterned membrane structure comprising a microporous membrane layer, wherein the microporous membrane layer includes a plurality of flow lanes, the flow lanes are separated by hydrophobic separation channels, and the flow lanes and hydrophobic separation channels form a pattern which may be repetitive, and a method for manufacture of the patterned membrane structure. The patterned membrane structure according to the present invention represents an industrial scale precursor of membranes such as a multiparameter lateral flow membrane comprising separated flow lanes.

BACKGROUND OF THE INVENTION

In modern biochemical analytics, immunoassays are routinely used to detect the presence or concentration of various substances, often referred to as ligands or analytes, in biological fluids such as blood, urine or saliva but also in a variety of other samples for example food extracts, surface water and else. In a solid phase immunoassay, a binding agent, typically an antibody which is specific for the ligand to be detected, is immobilized on a solid support. A test fluid that may comprise the ligand to be detected is contacted with the solid support and a complex between the binding agent and the ligand is formed in case the ligand is present. In order to make the complex visible, labelled antibodies may be used that bind to the complex followed by visual detection of the labelled antibody bound to the complex. Alternatively, an immunoassay is put together with a readout following a competitive reaction. To do so, the analyte per se is immobilized on a solid support and competes for the binding of the conjugated antibody with the analyte present in the sample. A sample rich in the defined analyte leads to a low absolute signal at the reaction area.

Porous materials such as nitrocellulose, nylon, cellulose acetate, glass fibers and other porous polymers have been employed as solid supports in solid phase immunoassays. In so-called lateral flow assays, a fluid to be tested for the presence of a ligand is applied to one end of a porous membrane layer and flows in lateral direction through the membrane under the action of capillary forces. The porous membrane comprises an immobilized binding agent that is capable of binding the ligand or the antibody against the ligand to be detected. The immobilized binding agent may be evenly distributed over the entire membrane. Typically, however, the immobilized binding agent is located in defined test or detection zones in the membrane, usually in narrow reaction areas that have been applied by means of contact or inkjet printing or other dispensing techniques.

In a lateral flow test, a thin layer of microporous material with immobilized binding agent may be supported on a liquid-impermeable layer to provide sufficient rigidity to the fragile microporous material layer. Usually a layer of microporous material with a thickness in the range of from about 80 to 200 µm is supported on a liquid-impermeable support layer, commonly referred to as "membrane backing" or "backing card".

Furthermore, a lateral flow immunoassay device, typically in the form of a test strip, includes, in the direction of lateral flow, a prefilter pad, a conjugate pad, a lateral flow membrane as described above, and an adsorbent pad.

In order to accommodate the need for testing multiple ligands or analytes (parameters) in a liquid sample with one test strip, lateral flow test strips or devices including more than one reaction area have been developed. Such lateral flow test strips and devices are based on patterned membranes and can be used in many fields of test and assay applications such as performing lateral flow immunoassays (e.g. for food technology, diagnosis).

Users expect results obtained by using different patterned membrane based assays or tests to be reproducible and comparable. That is, the obtained result should be independent from the specific manufacturing conditions of an individual lateral flow test strip or device. Thus, high homogeneity between different lots of patterned membranes represents an indispensable premise for quality, reproducibility and exactness of the results obtained by using a patterned membrane based assay or test.

However, lateral flow test strips and the underlying patterned membranes according to the state of the art vary significantly with regard to their respective geometric dimensions (e.g. the dimensions of the separation channels) and other structural parameters. These differences can be attributed to the variance of the manufacturing conditions by which state of the art patterned membranes are obtained.

Conventionally, each lot of patterned membranes for a certain kind of assay or test is produced as a lot of small individual membranes in a small quantity under varying parameters, i.e. by applying specific techniques under specific conditions of a specific manufacturer. The differences between the manufacturing conditions result in substantially varying product characteristics. Thus, the degree of comparability and conformity between patterned membranes from different lots and manufacturers is intolerably compromised.

Thus, there is a need for increasing the structural conformity of patterned membranes in order to obtain patterned membrane based assays having high quality, reproducibility and comparability.

BRIEF SUMMARY OF THE INVENTION

In view of the above, the technical problem underlying the present invention is to provide a precursor for a patterned membrane and a process for producing the same which should allow to efficiently produce large quantities of patterned membranes having high structural conformity.

According to the present invention, the above-described technical problem is solved by providing a patterned membrane structure in the form of a roll or sheet of industrial scale, comprising a microporous membrane layer, wherein the microporous membrane layer includes a plurality of flow lanes, the flow lanes are separated by hydrophobic separation channels, and the flow lanes and hydrophobic separation channels form a pattern.

Due to the specific form of the patterned membrane structure, i.e. an industrial scale roll or industrial scale sheet, the pattern of the patterned membrane structure according to the present invention can be formed with high precision and patterned membranes having high conformity can be produced efficiently and in large quantities.

In particular, since the patterned membrane structure has the form of a roll or a sheet of industrial scale, it can be produced by using industrial scale equipment which allows to produce the patterned membrane structure in a very precise and uniform manner. Contrary thereto, small-scale equipment used for the conventional production of patterned membranes does not provide the same degree of precision. Moreover, conventional small-scale equipment does not allow the production of large quantities of patterned membranes. Although patterning the surface of heavy, bulky and large unpatterned membrane structures such as rolls or sheets was considered to be imprecise and not feasible, it has surprisingly been found that industrial scale precursors allow the production of patterned membranes with excellent precision and in high quantities.

BRIEF DESCRIPTION OF THE DRAWINGS

FIG. 6A displays a single pattern. FIG. 6B displays the pattern of FIG. 6A as a repetitive pattern on a membrane roll. FIG. 6C displays the pattern of FIG. 6A as a repetitive pattern on a membrane sheet.

DETAILED DESCRIPTION

Figure 3:
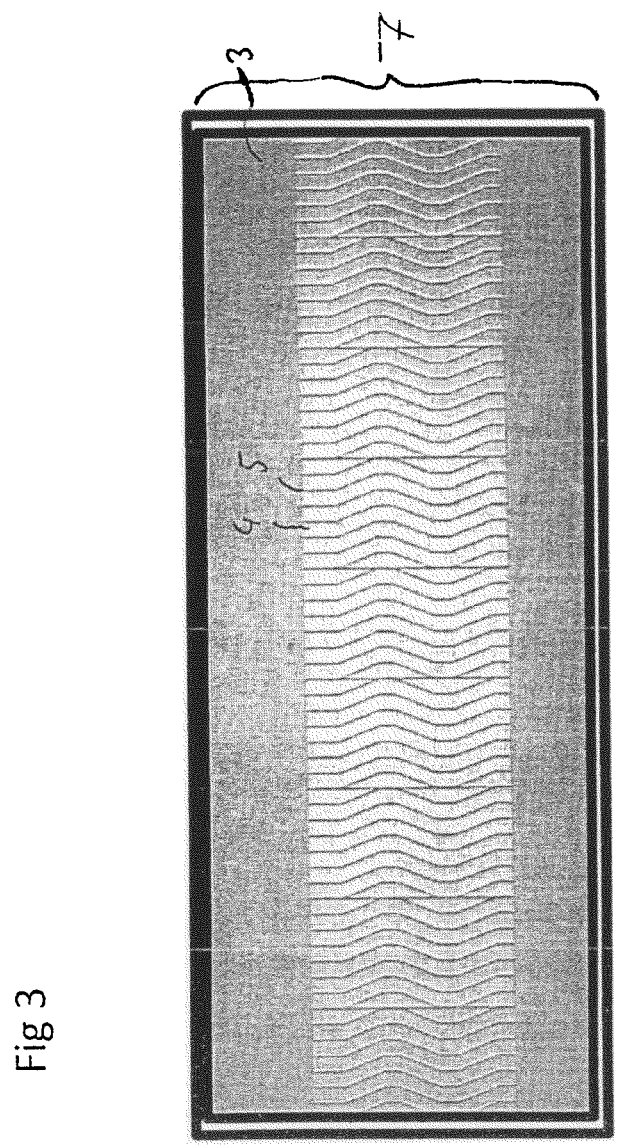
FIG. 3 shows a patterned membrane structure (7) according to the present invention in the form of a sheet before cutting to obtain single multiparameter strips.
Figure 4:
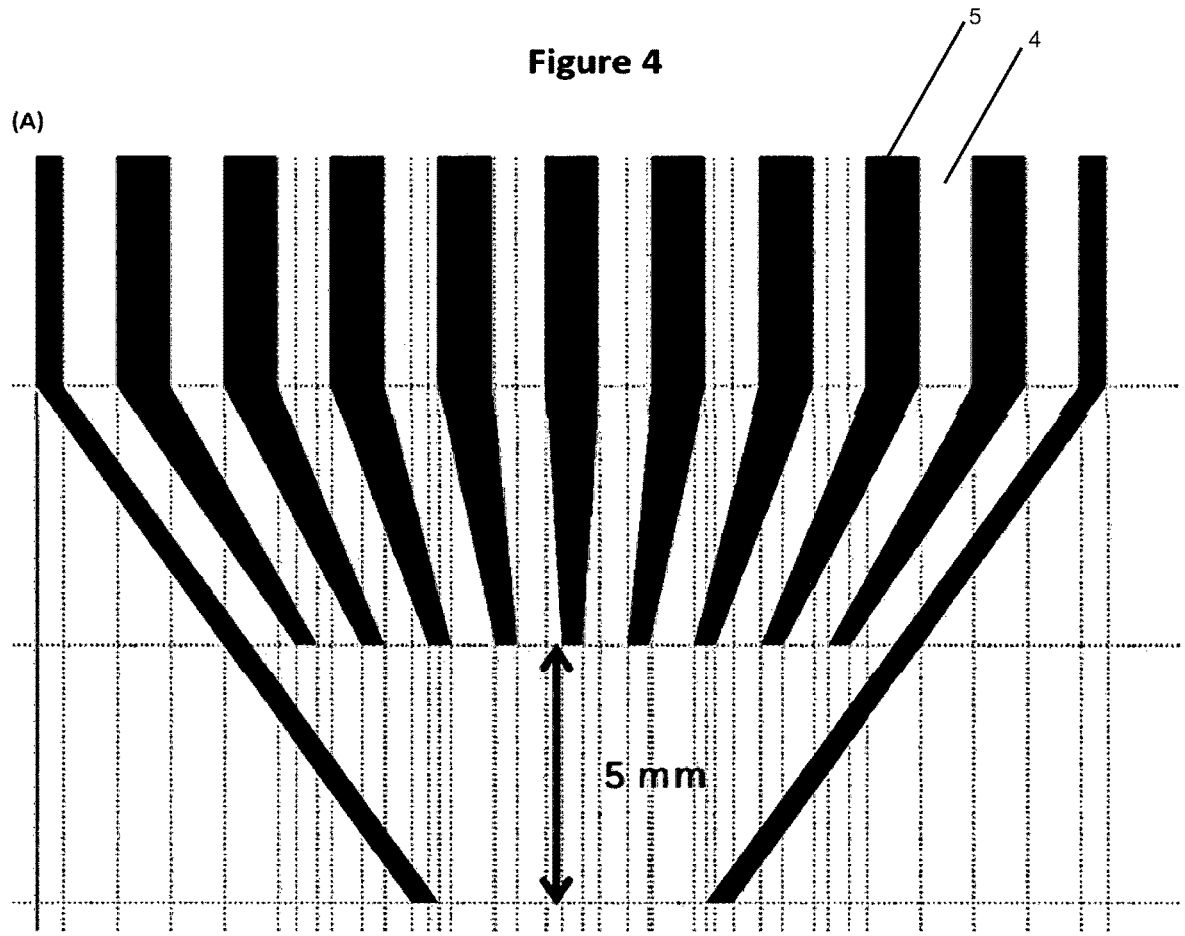
FIG. 4(A) shows a pattern having flow lanes 4 separated by separation channels 5 according to a preferred embodiment.
In FIG. 4(B), a patterned membrane structure including a repetitive pattern, i.e. the repeated pattern of FIG. 4(A), is displayed. A lateral flow membrane having the pattern of FIG. 4(A) can be obtained by processing, e.g. cutting, the membrane structure displayed in FIG. 4(B).
Figure 4:
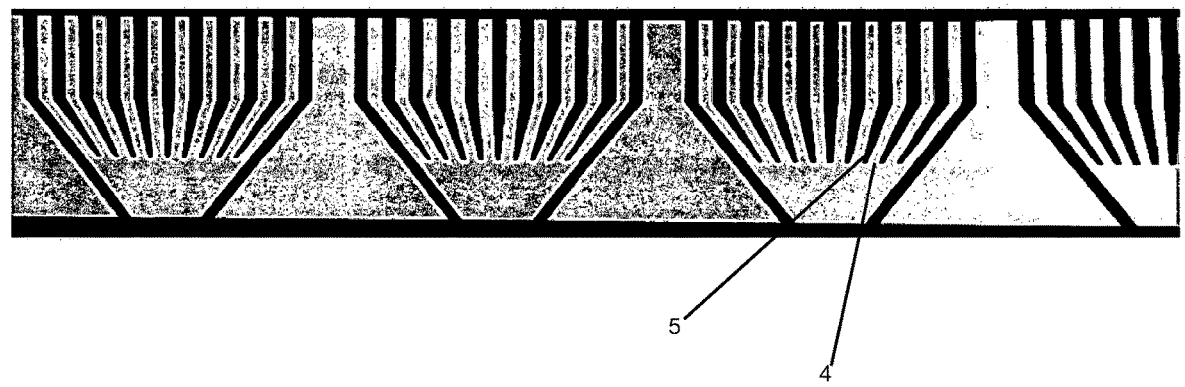
Figure 5:
FIG. 5(A) to (C) show three preferred embodiments of repetitive patterns including flow lanes (4) and separation channels (5).
Figure 5:
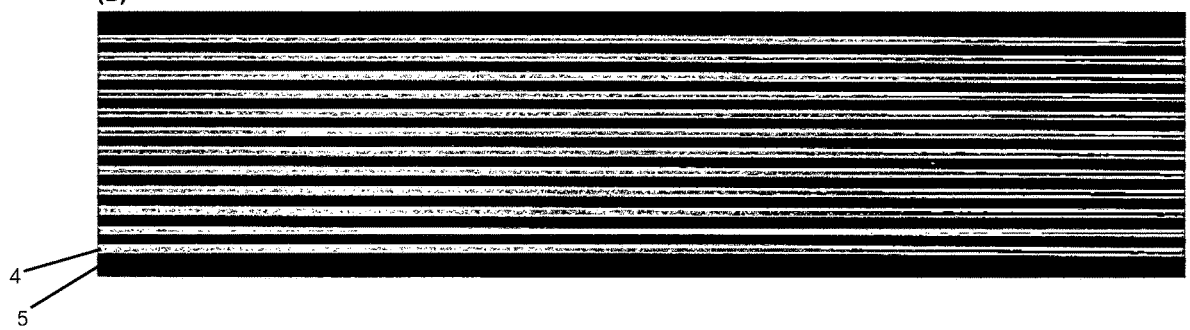
Figure 5:
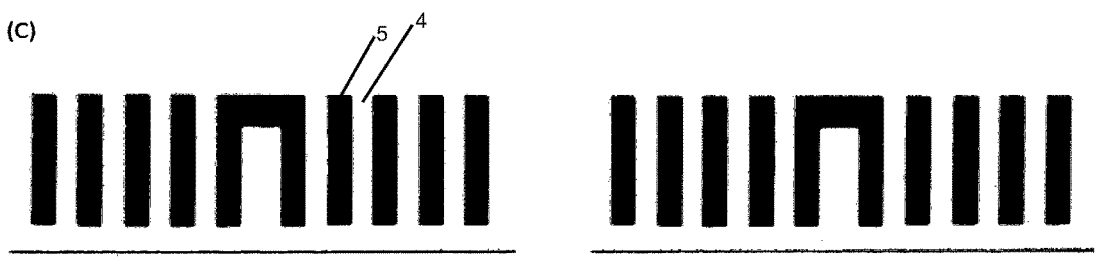
Figure 6:
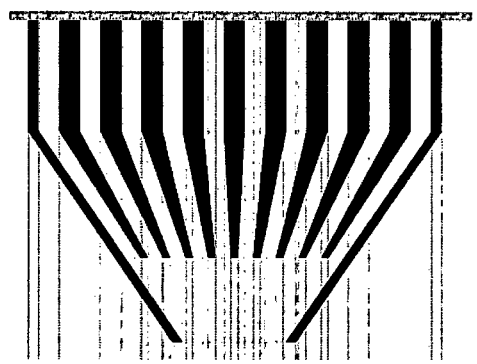
FIG. 6 A, B, C show a top view of a lateral flow membrane obtainable by processing a patterned membrane structure according to the present invention.
Figure 6:
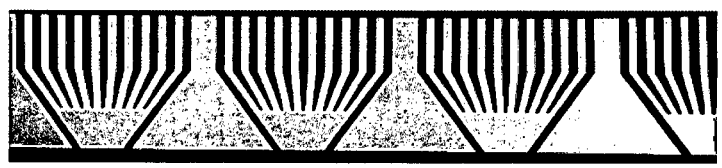
Figure 6:
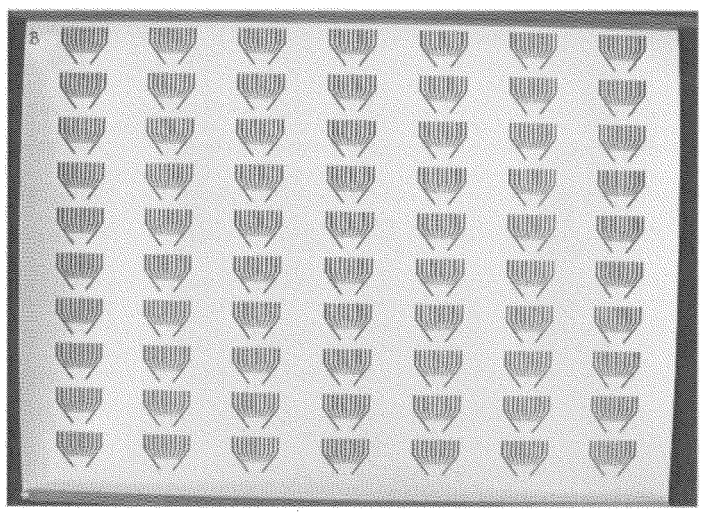
Figure 7:
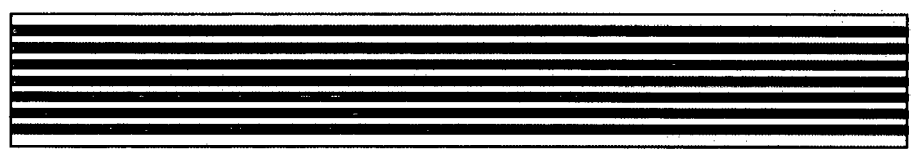
FIG. 7 shows a top view of a lateral flow membrane obtainable by processing a patterned membrane structure according to the present invention in the lateral flow direction. This pattern consists of alternating nitrocellulose-containing (NC) lanes and hydrophobic channels.
Figure 8:
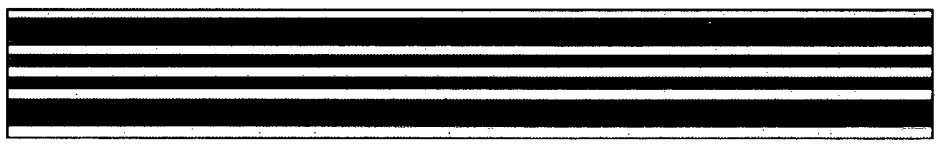
FIG. 8 shows a patterned membrane structure according to the present invention in the form of a membrane roll in the unwound state before cutting
Figure 9:
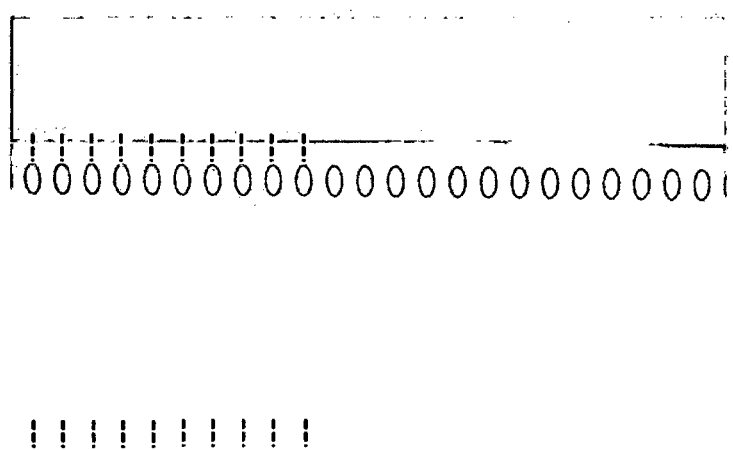
FIG. 9A shows a patterned nitrocellulose membrane laminated on a backing card. The nitrocellulose membrane exhibits a patterned structure resulting in a narrowing of the upper membrane segment within the lateral flow strip as well as a test and control line (FIG. 9B).
Figure 9:
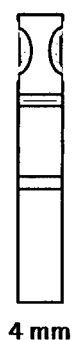
Figure 10:
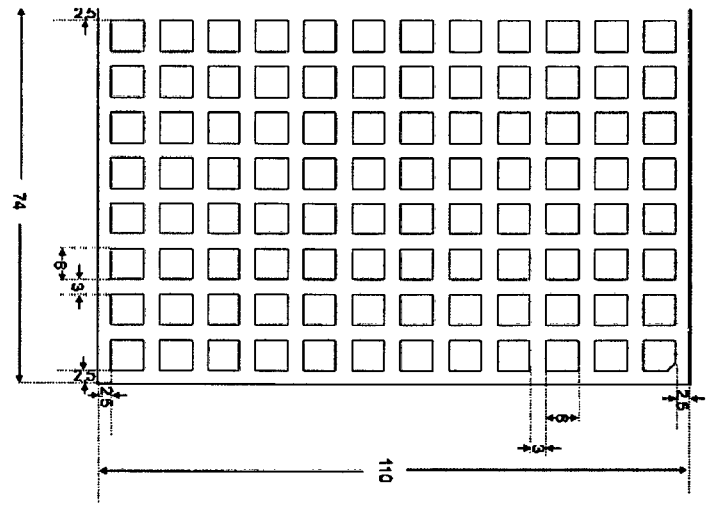
FIG. 10 is a diagram of a nitrocellulose sheet laminated on a solid support and structured into nitrocellulose patches corresponding to the dimension of the wells of a 96 microtiter plate.
Figure 11:
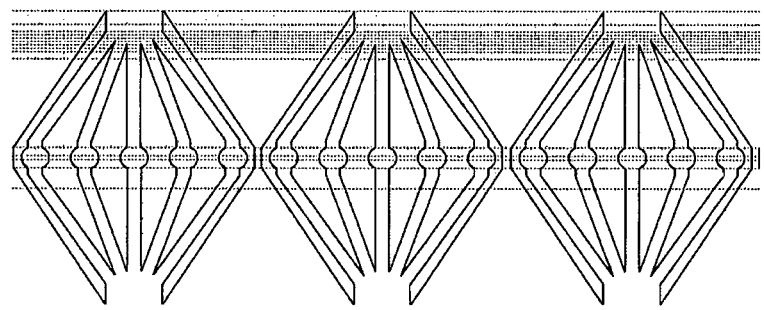
FIG. 11 is a diagram depicting a nitrocellulose membrane with a repetitive pattern of a multiparameter strip in a conical configuration with a common sample reservoir and 5 independent readouts.
Figure 12:
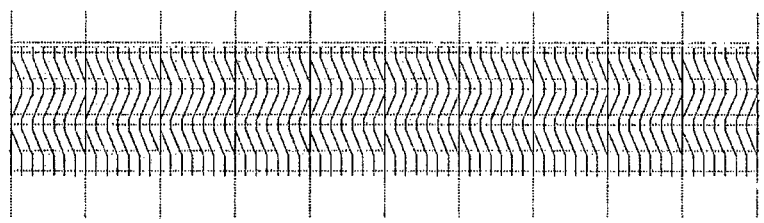
FIG. 12 is a diagram depicting a nitrocellulose membrane patterned with alternating hydrophobic channels and nitrocellulose lanes enabling multiple readouts for a given individual strip.

A "pattern" shall mean a specific structure on a membrane formed by one or more flow lanes and one or more separation channels. An example of a pattern is given in FIG. 3 by the channel indicated with reference numeral 4 including the adjacent separation channel(s), regarded in isolation from the other channels. Further exemplary embodiments of (repetitive) patterns are displayed e.g. in FIGS. 1, 4 to 12 and 14.

A repetitive pattern is formed by repeating a pattern. FIGS. 3 to 12 and 14 display various membrane structures having repetitive patterns.

A "separation channel" shall be understood as the part of a pattern or repetitive pattern which has a lower surface level than the rest of the membrane. The separation channel confines the area of liquid flow of the adjacent flow lane(s). The separation channel can be non-wetting and/or hydrophobic. A separation channel can have the same width along the direction of flow (isomorphic) or a changing width along the direction of flow. It can be straight, curved or otherwise formed.

A "flow lane" is the one or several elements of a pattern or repetitive pattern in which the flow of a liquid can take place. A flow channel can have the same width along the direction of flow (isomorphic) or a changing width along the direction of flow. It can be straight, curved or otherwise formed.

The flow lanes and separation channels can form a repetitive pattern built up of at least one pattern. It is possible to cut the repetitively patterned membrane structure into a plurality of membranes having the same pattern of flow lanes and separation channels. A repetitive pattern can be deconstructed into a plurality of similar patterns. In addition, a repetitively patterned membrane structure allows to obtain a plurality of membranes ideally having the same pattern of one or more flow lanes and one or more separation channels e.g. by cutting the membrane structure.

The repetitive pattern comprises one repeated pattern assembled together by a specific pattern or two or more repeated patterns assembled by more than one pattern. When the repetitive pattern includes more than one different pattern, a plurality of membranes having two or more different patterns of flow lanes and hydrophobic separation channels can be obtained by cutting the patterned membrane structure.

The at least one repetitive pattern of the membrane structure may occupy the entire width of the patterned membrane structure, especially when the repetitively patterned membrane structure has the form of a roll. In this case, the repetitively patterned membrane structure, which may also have the form of a sheet, can be fabricated into a plurality of membranes by carrying out only one cutting operation between two adjacent (repeated) patterns along the width direction of the membrane structure.

According to a preferred embodiment, the deviation of the pattern from a predetermined position is at most ±50 μm, preferably at most ±40 μm, more preferably at most ±30 μm. According to another preferred embodiment, the individual patterns forming the repetitive pattern of the patterned membrane structure according to the present invention deviate from each other by at most ±100 μm, preferably at most ±80 μm, more preferably at most ±60 μm. A pattern deviates from a predetermined position or another pattern when there are non-overlapping sections of the pattern and the predetermined position/the other pattern.

The patterned membrane structure according to the present invention preferably has a maximum length dimension of at least 10 cm, preferably at least 30 cm, more preferably at least 50 cm, and especially preferably at least 1 m. When the maximum length dimension (i.e. the longest dimension in length units) is at least 10 cm, the patterned membrane structure can be produced in large numbers on an industrial scale. Moreover, a considerable number of membranes can be produced by further processing (e.g. cutting) the patterned membrane structure. For instance, the patterned membrane structure can be processed to a lateral flow membrane comprising a microporous membrane layer for lateral flow of a liquid through the microporous membrane layer. Such lateral flow membranes can be used in multiparameter immunoassay devices.

According to one embodiment of the present invention, the (repetitively) patterned membrane structure has the form of a roll. The roll is formed by winding up the membrane structure. Preferably, the roll is formed by winding up a rectangularly shaped ribbon of the (repetitively) patterned membrane structure. The form of a roll allows easy storage, transportation and processing of the patterned membrane structure. Preferably, the (unwound) roll has a length of 50 to 200 m, preferably 50 to 100 m, and a width of 8 to 100 mm, preferably 20 to 35 mm.

According to another embodiment of the present invention, the (repetitively) patterned membrane structure has the form of a sheet. The form of a sheet allows easy storage and transportation of the patterned membrane structure. Preferably, the sheet has a length of 30 to 60 cm and a width of 30 to 60 cm. For instance, the sheet may be in the shape of a square having a side length of 30 to 60 cm, preferably 45 to 55 cm, for example 50 cm. The sheet may also be in the shape of a rectangle having a length of 40 to 70 cm, preferably 50 to 60 cm, and a width of 5 to 50 cm, preferably 10 to 16 cm.

According to a further preferred embodiment, the (repetitively) patterned membrane structure has the form of an ellipse. The length of the ellipse's major axis preferably ranges from 5 to 50 cm, more preferably 15 to 40 cm, and the length of the ellipse's minor axis preferably is 1/10 to 2/3 of the length of the major axis.

According, to yet another preferred embodiment, the (repetitively) patterned membrane structure has the form of a circle. The circle preferably has a radius of 5 to 25 cm, preferably 10 to 15 cm.

By processing the (repetitively) patterned membrane structure according to the present invention, e.g. by cutting, a multiparameter lateral flow membrane can be obtained. Such a multiparameter lateral flow membrane as shown e.g. in FIGS. 1, 2, 6, 7, 8, 11 and 12 is an elongate arrangement of a microporous membrane layer, preferably supported on a liquid-impermeable support layer. The multiparameter lateral flow membrane is suitable for lateral flow of a liquid through the microporous membrane layer under the action of capillary forces and is typically used in lateral flow immunoassays for detecting a ligand or analyte in a test fluid that flows laterally through the microporous membrane layer.

According to the present invention, the microporous membrane layer has a plurality, i.e. two or more, flow lanes, as shown in FIGS. 1 to 3, 6 to 8, 11 and 12.

The width of the flow lanes is not specifically restricted, however, is usually in the range of from 1 mm to 4 mm, preferably in the range of from 2 mm to 3 mm.

Figure 1:
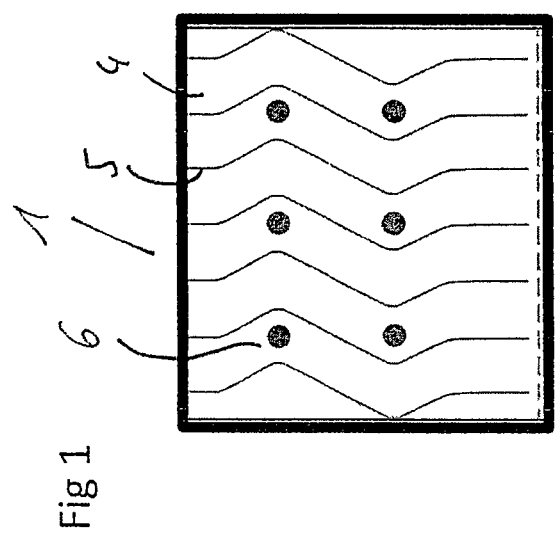
FIG. 1 shows a top view of a lateral flow membrane obtainable by processing a patterned membrane structure according to the present invention.
Figure 2:
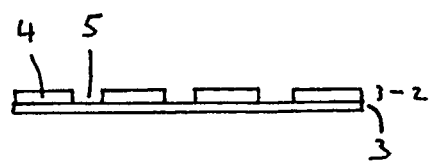
FIG. 2 shows a cross-sectional view of a lateral flow membrane obtainable by processing a patterned membrane structure according to the present invention in the lateral flow direction.

Furthermore, the shape of the flow lanes is not specifically restricted. However, preferably, the shape of the flow lanes is selected from the group consisting of straight lanes, zig-zag-shaped lanes and meander-shaped lanes. More preferably, the shape of the flow lanes is selected from the group consisting of zig-zag-shaped lanes and meander-shaped lanes, as shown in FIG. 1 (zig-zag-shaped lanes) and FIGS. 3 and 12 (meander-shaped lanes).

According to the present invention, the flow lanes are separated by separation channels, as shown in FIGS. 1 to 3, 6 to 8, 11 and 12. Preferably, each of the plurality of flow lanes comprises a detection zone including one binding agent, as shown for e.g. in FIG. 1, such that each reaction zone is supplied with the test liquid by its own flow lane (cf. FIG. 11). In one embodiment of the invention, each of the flow lanes can comprise a reaction zone and at least some of the several flow lanes can comprise identical or different binding agent(s). Due to said separation, each reaction zone of each membrane obtained by processing the (repetitively) patterned membrane structure (e.g. by cutting) will receive exactly the same amount and the same quantity of sample and conjugate solution, which results in an improved assay sensitivity and signal intensity for each detection spot. The detection spot can be provided on the (repetitively) patterned membrane structure before it is processed to a membrane or can be provided on the membrane obtained by processing the (repetitively) patterned membrane structure.

According to a preferred embodiment of the present invention, each reaction zone has a diameter or dimension of from 0.5 mm to 3 mm, preferably of from 1 mm to 2 mm. Furthermore, the reaction zone preferably has a circular shape, but could also be in the shape of small lines (jetted non-contact spotting equipment).

According to a preferred embodiment of the present invention, the separation channels have a width of from 0.1 mm to 3 mm, preferably of from 0.15 mm to 1.5 mm.

The microporous membrane layer may be made of any suitable microporous material for lateral flow membranes. Such materials are known in the art and include nitrocellulose, nylon, cellulose acetate, PES (polyethersulfone), PVDF (polyvinylidenfluoride), cross-linked dextran and other porous polymers. Preferably, the microporous membrane layer is a nitrocellulose layer. Nitrocellulose membrane layers for lateral flow assays are well-known in the art and are composed of interconnected nitrocellulose rods in a sponge-like structure.

Liquid-impermeable support layers are well-known in the art and are often referred to as "backing". Suitable support layers include polymeric materials such as for example polyester, polypropylene, polyethylene, acrylic (co)polymers, vinyl-acrylic polymers, polycarbonates and heteropolysaccharides.

According to a preferred embodiment of the present invention, each of said two or more flow lanes further comprises a control zone including a binding agent downstream of the reaction zone. Control zone of individual lanes can comprise different reagents. This control zone usually will bind all conjugate reagent or particle in excess.

The major role of the control zone is to indicate that the liquid has been transported into the designated lane. The selected reagent combination will necessarily lead to a positive readout, independent of the outcome at the test zone. For example, an anti-mouse immunoglobulin purified from rabbit can be printed at a final concentration of 1 mg/ml.

According to a preferred embodiment of the present invention, each control zone has a diameter or dimension in the same range as the test zone, i.e. from 0.5 mm to 3 mm, preferably of from 1 mm to 2 mm.

In order to visualize the complex between the binding agent and the ligand or analyte formed in the detection zones, detectable markers such as for example immunolabels are typically used. Most often, the liquid to be analyzed first flows through a so-called conjugate pad before it flows through the lateral flow membrane. The conjugate pad comprises a moveable conjugate of detectable marker and a detection agent, i.e. an agent that can bind to the ligand or analyte but different from the binding agent. If the liquid to be analyzed flows through the conjugate pad, the conjugate binds to the ligand and the ligand/conjugate complex flows with the liquid through the membrane layer. In the membrane layer the ligand-conjugate complex binds to the immobilized binding agent. The moveable conjugate is usually specific to one analyte. Consequently in a multiparameter test several conjugate reagents are mixed and applied on the conjugated pad through the whole pad width. Another option would be to spray the individual conjugated reagents at regular interval on the conjugated pad. The width of the interval corresponds to the width of the flow lanes resulting in a higher concentration of the desired conjugate in a specified lane. This option may also reduce the amount of conjugate necessary to generate a visible signal because of the higher reagent concentration for the defined area. Alternative to a conjugate pad upstream of the lateral flow membrane, the lateral flow membrane per se may comprise at least one conjugate zone that comprises a moveable conjugate of detectable marker and detection agent. Such conjugate zones are located upstream of a detection spot. In this case only the conjugate specific to the ligand on the detection zone will flow in the dedicated lane without any loss in the other lanes. Suitable detectable markers that can be used in this respect are not particularly limited and are known in the art. They include for example latex beads of different colors or fluorescent dyes as well as gold nanoparticles.

Thus, according to a preferred embodiment of the present invention, each of said two or more flow lanes further comprises at least one conjugate spot that comprises a moveable conjugate of detectable marker and detection agent upstream of the detection spot. The area of the membrane or the patterned membrane structure used to deposit the conjugated reagent(s) can be slightly larger (1 mm) than the here defined flow lane.

According to a preferred embodiment of the present invention, the binding agents are selected from the group consisting of proteins and peptides in particular antibodies and aptamers.

According to the present invention, the method for the manufacture of the (repetitively) patterned membrane structure comprises the steps of (A) providing an unpatterned membrane structure comprising a microporous membrane layer;
(B) supplying the unpatterned membrane structure to a means for patterning;
(C) patterning the unpatterned membrane structure, such that the microporous membrane layer includes a plurality of flow lanes, wherein the flow lanes are separated by separation channels and the flow lanes and separation channels form a pattern. Preferably, a repetitive pattern is formed.

In a preferred embodiment, the method further comprises, after step (B) and prior to step (C), a step of (Ca) adjusting the position of the means for patterning and/or the unpatterned membrane structure. Preferably, step (Ca) is carried out by determining whether the position of the means for patterning and/or the position of the unpatterned membrane structure complies with a desired position (i.e. has the correct position), and, in the negative, correcting the position of the means for patterning and/or the position of the unpatterned membrane structure so as to comply with the desired position.

The step of determining whether the position is correct can be carried out by a detection means such as a camera. The detection means determines the position of the unpatterned membrane structure relative to the means for patterning. If the position is not correct, either or both of the position of the means for patterning and the position of the unpatterned membrane structure is/are corrected, e.g. by virtue of an x-y displacement unit on which the means for patterning (such as a laser) is mounted.

Preferably, the unpatterned membrane structure includes reference points. In addition, it is preferred that step (Ca) is carried out by adjusting the position of the means for patterning based on the reference points. The step of determining whether the position is correct is preferably carried out by a detection means such as a camera. The detection means may determine the position of the unpatterned membrane structure relative to the means for patterning by detecting the position of the reference points. If the position is not correct, either or both of the position of the means for patterning and the position of the unpatterned membrane structure is/are corrected, e.g. by virtue of an x-y displacement unit on which the means for patterning (such as a laser) is mounted.

Due to step (Ca), the patterned membrane structure can be produced both rapidly and with high precision. For instance, it is possible to obtain patterned membrane structures having a deviation of each of the individual patterns from a predetermined position of at most ±50 µm, preferably at most ±40 µm, more preferably at most ±30 µm, and/or a deviation of the individual patterns from each other by at most ±100 µm, preferably at most ±80 µm, more preferably at most ±60 µm.

The unpatterned membrane structure provided in step (A) of the present method is a common membrane structure which can be manufactured in a known manner. Preferably, the unpatterned membrane structure is supported on a liquid-impermeable support layer as described above. Typically, an unpatterned membrane structure can be manufactured by first providing a liquid-impermeable support layer and then applying a solution of the material of which the microporous membrane layer is composed in a suitable solvent on the support layer. The solvent is then evaporated and an unpatterned membrane structure including a microporous membrane layer supported on the liquid-impermeable support layer is obtained.

In step (B), the unpatterned membrane structure is supplied to a means for patterning. Means and methods for patterning are not particularly restricted and include mechanical and chemical methods such as etching, wax printing, photolithography, plasma and laser treatment. A preferred method for patterning is laser treatment. A preferred means for patterning is/are one or more laser devices.

According to step (C) of the present method, the (repetitive) patterning of the unpatterned membrane structure to form hydrophobic separation channels is carried out, such that a plurality of isomorphic flow lanes is provided.

According to a preferred embodiment, step (C) includes one or more of the group consisting of (C1) laser etching, (C2) chemical etching (C3) mechanical treatment, and/or (C4) printing. That is, (repetitively) patterning of the unpatterned membrane structure may be carried out by one of the aforementioned methods (C1) to (C4) or any combination thereof. Preferably, patterning is carried out by laser-etching.

Preferably, the microporous membrane layer is treated with laser-etching such that the material of the microporous membrane layer is removed from the liquid-impermeable support layer and a plurality of isomorphic flow lanes is formed, which are separated by borderlines reaching down to the exposed material of the liquid-impermeable support layer. A similar effect can be obtained by (C2) chemical etching (C3), mechanical treatment, and/or (C4) printing.

A laser etching process can be achieved for example by the use of a Nd:YVO$_4$ solid-state laser having picosecond pulses, especially at a wavelength of 532 nm and a pulse length of 12 psec, a pulse energy of 10 mJ and a pulse frequency of 10 kHz. Alternative laser etching process with Nd YAG or CO$_2$ laser have also led to successful structuring of nitrocellulose membrane.

According to a preferred embodiment, the method for manufacture according to the present invention includes the steps of:
(A) providing an unpatterned membrane structure comprising a microporous membrane layer;
(As1) slitting the unpatterned membrane structure along its length direction and/or width direction, thereby obtaining a slit unpatterned membrane structure;
(Bs) supplying the slit unpatterned membrane structure to a means for patterning;
(Cs) patterning the slit unpatterned membrane structure such that the microporous membrane layer includes a plurality of flow lanes, wherein the flow lanes are separated by separation channels and the flow lanes and separation channels form a pattern. Preferably, a repetitive pattern is formed.

According to the above preferred embodiment, a step of slitting the unpatterned membrane structure along its length and/or width direction is carried out prior to patterning the slit unpatterned membrane structure. A narrower width of the membrane structure facilitates positioning the pattern on the membrane with high precision.

Of course, slitting can also be carried out after (repetitive) patterning. Two or more slitting steps may be carried out before and after (repetitive) patterning. Thus, a preferred embodiment of the present method comprises the step of (Ds1) slitting the (repetitive) patterned membrane structure along its length direction and/or width direction, thereby obtaining a slit (repetitively) patterned membrane structure.

In a preferred embodiment of the method for manufacture according to the invention; the slit unpatterned membrane structure has the form of a roll and the method further comprises the steps of
(As2) winding up the slit unpatterned membrane structure;
(As3) unwinding the slit unpatterned membrane structure.

In a further preferred embodiment of the method for manufacture according to the invention, the slit patterned membrane structure has the form of a roll and the method further comprises the steps of
(Ds2) winding up the slit patterned membrane structure;
(Ds3) unwinding the slit patterned membrane structure.

After each slitting step, the slit (un)patterned membrane may be wound up to the form of a roll, followed by unwinding the roll. When the slit (un)patterned membrane structure has the form of a roll, it can be easily stored and transported. Moreover, the form of a roll allows fast processing of the membrane structure so that the patterned membrane structure and the final membrane can be produced at high throughput. Furthermore, a slitting and winding operation can be carried out at a first time and a first place, the membrane can then be stored and/or transported, and an unwinding and patterning or a further processing (e.g. cutting into individual membranes) operation can be carried out at a second time and a second place. Thus, immediate processing of the (un)patterned membrane structure is not necessary, providing a highly flexible manufacturing method.

In a similar manner, after each slitting step, the slit (un)patterned membrane may be piled up to a stack of sheets, followed by unpiling the stack. When the slit (un)patterned membrane has the form of a stack of sheets, it can be easily stored and transported. Accordingly, a slitting and piling operation can be carried out at a first time and a first place, the membrane can then be stored and/or transported, and an unpiling and patterning or a further processing (e.g. cutting into individual membranes) operation can be carried out at a second time and a second place.

In particular, in a preferred embodiment of the method for manufacture according to the invention, the slit unpatterned membrane structure has the form of a sheet and the method further comprises the steps of
(As4) piling up the slit unpatterned membrane structure to obtain a stack of sheets;
(As5) unpiling the stack of sheets of the slit unpatterned membrane structure.

In a further preferred embodiment of the method for manufacture according to the invention, the slit patterned membrane structure has the form of a sheet and the method further comprises the steps of
(Ds4) piling up the slit patterned membrane structure to obtain a stack of sheets;
(Ds5) unpiling the stack of sheets of the slit patterned membrane structure.

According to the present invention, a patterned membrane structure in the form of a roll or sheet of industrial scale can be manufactured by placing an unpatterned membrane roll or sheet into an apparatus. Such an apparatus can be equipped with cutting tools, means for patterning, means for controlling the position of the sheet or roll such as mechanical structures, a camera or a laser marking. The means for positional control allow the control of the position of the membrane roll or membrane sheet.

After the membrane roll or membrane sheet has been fixed in or introduced into such an apparatus, the unpatterned membrane structure can be subjected to patterning, e.g. by using high precision engraving systems. Such engraving systems can be operated by computer driven control technology which allows high precision patterning. Such engraving systems can be laser systems, printers, photolithographic devices, chemical spraying devices or other suitable apparatuses. Thereby, it is possible to pattern the unpatterned structure, e.g. by engraving into the membrane surface any pattern, any number of one or several repetitive patterned membrane motif(s) (repetitive patterns) with high precision and conformity. The membrane structure including these motif(s)/pattern(s) can be carved out or sliced in order to obtain individual patterned membranes by a slicing device. Thus, the patterned membrane roll or sheet according to the present invention allows to provide large quantities of patterned membranes having highly homogenous structures.

The patterning of the membrane e.g. by a laser can be performed by a step-by-step process or by a continuous process. For the step-by-step process the membrane is moved forward to a table with particular dimensions (working range) e.g. of 10×16 cm). The membrane movement is stopped once the table is covered by an unpatterned membrane section and optionally fixed by a vacuum or by clamps. The laser or other means for patterning forms the pattern on the membrane surface. After the area of the membrane structure which covers the table, is covered by the pattern, the membrane roll is moved forward by the length dimension of the working range, i.e. the length of the table, in order to expose an unpatterned section of the membrane structure to the laser. The process continues until the whole membrane roll is covered with a pattern (i.e. patterned).

For the continuous process the membrane is moved continuously without interruption while the laser is patterning the membrane.

The present invention is further illustrated by the following examples, without being limited thereto.

Example A

Figure 13:
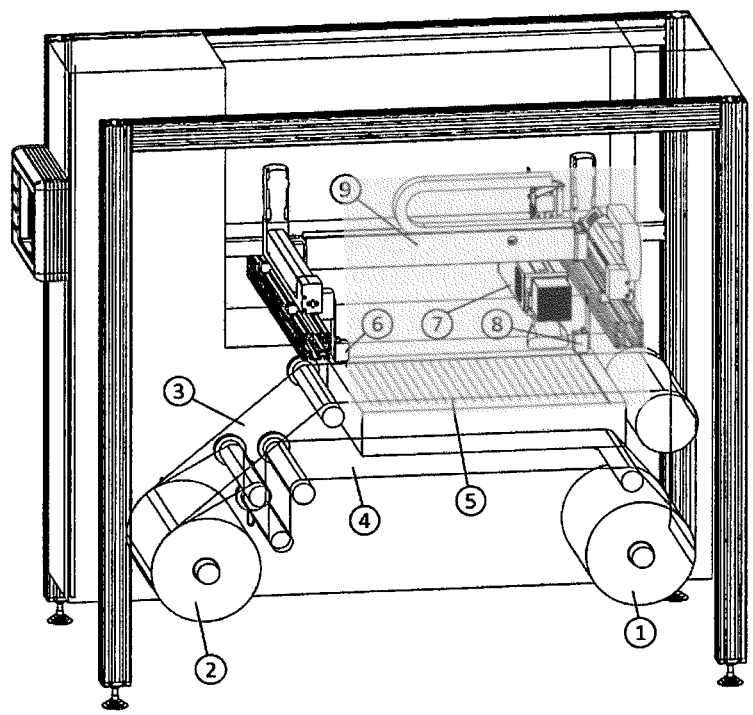
FIG. 13 is a diagram depicting an apparatus for manufacturing a patterned membrane structure according to the present invention. A membrane roll is introduced to be patterned. The apparatus is suited for processing membrane structures of varying width. Alternatively, sheets can be manually inserted or fed through an automated feeder. The reference numerals of FIG. 13 are as follows: 1: input of the membrane roll; 2: output of the patterned membrane roll; 3: patterned membrane; 4: interleaving paper; 5: vacuum table plate; 6: camera for positioning of the membrane roll in the forward direction; 7: laser; 8: camera for positioning of the membrane roll perpendicular to the forward direction; 9: x-y positioning of the laser.
Figure 14:
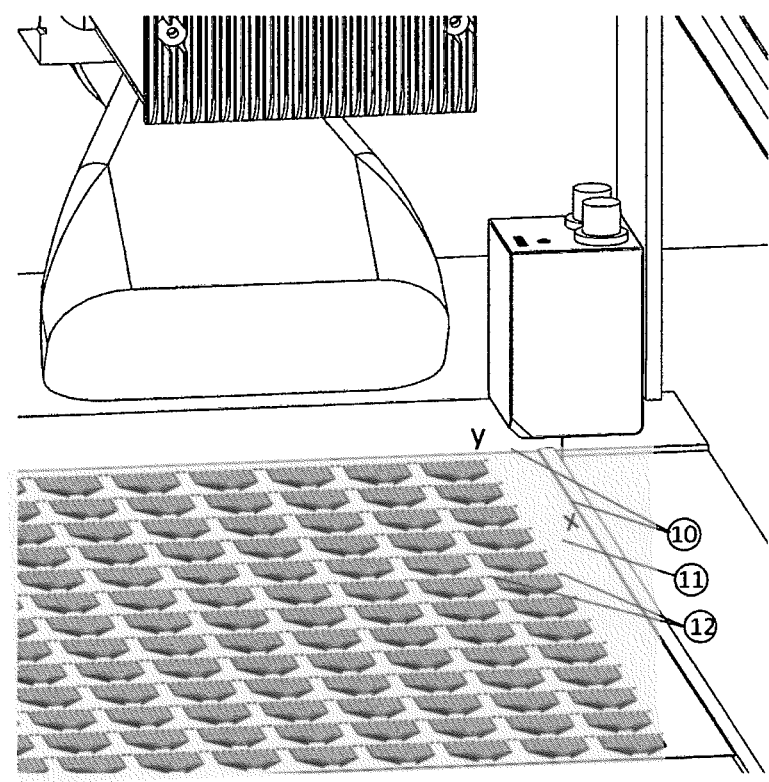
FIG. 14 is a diagram depicting a detailed view of the laser and camera of the device shown in FIG. 13. The reference numerals of FIG. 14 are as follows: 10: insertion of a membrane sheet/roll up to the x-y-limit stop; 11: membrane sheet with two reference points per repetitive pattern; 12: reference points for the positioning of the laser.

Patterned membrane structures according to the present invention were produced using the apparatus displayed in FIG. 13.

The device is capable of automatically introducing a given pattern on a membrane in the form of a roll or alternatively on a membrane sheet. The membrane can be fed into the apparatus and collected therefrom either manually or automatically. The dimensions of the reeding and stacking units can be adjusted according to the number of membrane samples being processed.

The defined pattern was applied to a membrane sample in a roll format as follows (e.g. FIG. 13): The membrane roll is mounted, positioned and spanned in the device (FIG. 13, #1), the membrane (FIG. 13, #3) and interleaving paper (FIG. 13, #4) are threaded through the device and fixed on a roll core (FIG. 13, #2). Once the web tension is set and the path above the vacuum table (FIG. 13, #5) is fixed horizontally, one or multiple laser(s) (FIG. 13, #7) can be positioned with the help of reference points (FIG. 14, #12) provided on the unpatterned membrane which are recognized by a head camera. All patterns and reference points (FIG. 14, #12) in the area which are accessible to the laser ("field of the laser(s)" or simply "field") can then be processed. Due to the positioning by the camera system, the precision of the pattern (deviation of the pattern from its predetermined position) can be as high as ±50 μm or even more precise.

Once the patterns in one laser field have been formed, the laser is positioned in a new field with the assistance of an x-y displacement unit. In that manner, the membrane can be patterned field by field resulting in completion of patterning of the current working range.

Through a programmed process and the control of a second camera (FIG. 13, #6), the membrane is wound and fixed according to the length of the working range (size of the (vacuum) table). The precise positioning of the laser is re-assessed according to the reference points and the patterning cycle is repeated.

Example B

Membrane rolls having a width between 15 and 500 mm and a length up to 200 m can be processed with the device described in Example A. The patterned membrane is wound up with an interleaving paper. The device is equipped with a deviating roller and a length compensator that allows the membrane structure and the interleaving paper to take independent paths during patterning. After patterning, the two paths converge and the two components (membrane structure and interleaving paper) are wound together. The paths of the membrane structure and the interleaving paper are controlled by an edge guide control. The positioning with a precision of ±50 μm or better is ensured by the use of a camera.

Example C

Membrane sheets with dimensions of up to 700×500 mm are patterned with the device described in Example A. The membrane sheets can be fed and collected either manually or automatically.

REFERENCE NUMBER LIST

1 lateral flow membrane
2 microporous membrane layer
3 support layer
4 flow lanes
5 separation channel, borderlines
6 detection spot, detection zones, reaction zone

The invention claimed is:

1. A patterned membrane structure in the form of a roll or sheet of industrial scale, comprising a microporous membrane layer, wherein
   the microporous membrane layer includes a plurality of flow lanes,
   the flow lanes run parallel and adjacent to one another and are separated by hydrophobic separation channels, wherein a first flow lane is separated by a single hydrophobic separation channel from an adjacent and parallel second flow lane, and
   the flow lanes and hydrophobic separation channels form a pattern,
   the flow lanes and hydrophobic separation channels are straight, zig-zag-shaped, or meander-shaped,
   the flow lanes are isomorphic lanes, and
   the pattern is formed by laser etching.

2. The patterned membrane structure according to claim 1, wherein the pattern is a repetitive pattern.

3. The patterned membrane structure according to claim 1, wherein the roll has
   a length of 50 to 200 m.

4. The patterned membrane structure according to claim 1, wherein the sheet has
a length of 30 to 60 cm and
a width of 30 to 60 cm.

5. The patterned membrane structure according to claim 1, wherein the microporous membrane layer is made of nitrocellulose.

6. The patterned membrane structure according to claim 1, wherein the microporous membrane layer is supported on a liquid-impermeable support layer.

7. A method for the manufacture of a patterned membrane structure according to claim 1, comprising the steps of:
(A) providing an unpatterned membrane structure comprising a microporous membrane layer;
(B) supplying the unpatterned membrane structure to a means for patterning;
(C) patterning the unpatterned membrane structure, such that the microporous membrane layer includes a plurality of flow lanes, wherein the flow lanes run parallel and adjacent to one another and are separated by separation channels and the flow lanes and separation channels form a pattern, the flow lanes and hydrophobic separation channels are straight, zig-zag-shaped, or meander-shaped, the flow lanes are isomorphic lanes, wherein a first flow lane is separated by a single hydrophobic separation channel from an adjacent and parallel second flow lane, and wherein the patterning is formed by laser etching.

8. The method for manufacture according to claim 7,
further comprising, after step (B) and prior to step (C), a step of (Ca) adjusting the position of the means for patterning and/or the unpatterned membrane structure.

9. The method for manufacture according to claim 8,
wherein the unpatterned membrane structure includes reference points and step (Ca) is carried out by adjusting the position of the means for patterning relative to the unpatterned membrane structure based on the reference points.

10. The method for manufacture according to claim 7, wherein step (C) includes one or more of the group consisting of chemical etching, mechanical treatment, and/or printing.

11. The method for manufacture according to claim 7, including the steps of:
(A) providing an unpatterned membrane structure comprising a microporous membrane layer;
(As1) slitting the unpatterned membrane structure along its length direction and/or width direction, thereby obtaining a slit unpatterned membrane structure;
(Bs) supplying the slit unpatterned membrane structure to a means for patterning;
(Cs) patterning the slit unpatterned membrane structure, such that the microporous membrane layer includes a plurality of flow lanes, wherein the flow lanes are separated by hydrophobic separation channels and the flow lanes and hydrophobic separation channels form a repetitive pattern.

12. The method for manufacture according to claim 11,
wherein the slit unpatterned membrane structure has the form of a roll and the method further comprises the steps of
(As2) winding up the slit unpatterned membrane structure;
(As3) unwinding the slit unpatterned membrane structure.

13. The method for manufacture according to claim 7, further comprising the step of:
(Ds1) slitting the patterned membrane structure along its length direction and/or width direction, thereby obtaining a slit patterned membrane structure.

14. The method for manufacture according to claim 13,
wherein the slit patterned membrane structure has the form of a roll and the method further comprises the steps of
(Ds2) winding up the slit patterned membrane structure;
(Ds3) unwinding the slit patterned membrane structure.

15. The patterned membrane structure according to claim 1, wherein the hydrophobic separation channels and the plurality of flow lanes alternate.

16. The patterned membrane structure according to claim 1, wherein the first flow lane comprises a first detection zone and the adjacent and parallel second flow lane comprises a second detection zone.

17. The patterned membrane structure according to claim 1, wherein each of the plurality of flow lanes comprises a detection zone.

18. A patterned membrane structure in the form of a roll or sheet of industrial scale, comprising a microporous membrane layer, wherein
the microporous membrane layer includes a plurality of flow lanes,
the flow lanes run parallel and adjacent to one another and are separated by hydrophobic separation channels, wherein the plurality of flow lanes are separated from each other along an entire length of each flow lane, and
the flow lanes and hydrophobic separation channels form a pattern,
the flow lanes and hydrophobic separation channels are straight, zig-zag-shaped, or meander-shaped,
the flow lanes are isomorphic lanes, and
the pattern is formed by laser etching.

* * * * *